United States Patent
Purcell et al.

(10) Patent No.: US 10,980,644 B2
(45) Date of Patent: Apr. 20, 2021

(54) EXPANDABLE CAGE

(71) Applicant: Astura Medical Inc., Carlsbad, CA (US)

(72) Inventors: Thomas Purcell, Carlsbad, CA (US); Greg Martin, Carlsbad, CA (US)

(73) Assignee: Astura Medical Inc, Carlsbad, CA (US)

( * ) Notice: Subject to any disclaimer, the term of this patent is extended or adjusted under 35 U.S.C. 154(b) by 110 days.

(21) Appl. No.: 16/447,803

(22) Filed: Jun. 20, 2019

(65) Prior Publication Data

US 2019/0388232 A1 Dec. 26, 2019

Related U.S. Application Data

(60) Provisional application No. 62/687,308, filed on Jun. 20, 2018.

(51) Int. Cl.
*A61F 2/44* (2006.01)
*A61F 2/30* (2006.01)
*A61F 2/28* (2006.01)
*A61F 2/46* (2006.01)

(52) U.S. Cl.
CPC .............. *A61F 2/447* (2013.01); *A61F 2/442* (2013.01); *A61F 2/28* (2013.01); *A61F 2/4611* (2013.01); *A61F 2002/30579* (2013.01)

(58) Field of Classification Search
CPC .......... A61F 2/44; A61F 2/4455; A61F 2/447; A61F 2002/30537–30545; A61F 2002/30553–30556
See application file for complete search history.

(56) References Cited

U.S. PATENT DOCUMENTS

| | | |
|---|---|---|
| 2010/0049324 A1 | 2/2010 | Valdevit |
| 2011/0035011 A1 | 2/2011 | Cain |
| 2013/0211525 A1* | 8/2013 | McLuen ................. A61F 2/442 623/17.16 |
| 2013/0274883 A1* | 10/2013 | McLuen ................... A61F 2/28 623/17.16 |
| 2014/0031938 A1 | 1/2014 | Leashmann et al. |
| 2014/0039622 A1* | 2/2014 | Glerum ................... A61F 2/446 623/17.15 |
| 2014/0277500 A1* | 9/2014 | Logan ..................... A61F 2/447 623/17.16 |
| 2015/0073552 A1 | 3/2015 | To et al. |

(Continued)

OTHER PUBLICATIONS

International Search Report and Written Opinion in PCT Application No. PCT/US2019/038313 dated Aug. 30, 2019.

*Primary Examiner* — Eduardo C Robert
*Assistant Examiner* — Michelle C Eckman
(74) *Attorney, Agent, or Firm* — Michael R Shevlin

(57) ABSTRACT

An expandable cage for placement between adjacent vertebrae having two or more upper and lower end plates having compound-angled slots, ramps or rails, and a drive means having corresponding compound-angled slots, ramps or rails configured to slidingly engage the compound-angled slots, ramps or rails of the two or more upper and lower end plates, wherein movement of the drive means in a first direction moves the two or more upper and lower end plates away from each other both vertically and horizontally to expand both a height and a width of the expandable cage from a collapsed state to an expanded state.

16 Claims, 8 Drawing Sheets

(56) References Cited

U.S. PATENT DOCUMENTS

2017/0216046 A1\* 8/2017 Greenhalgh ............ A61F 2/447
2017/0224505 A1\* 8/2017 Butler ....................... A61F 2/44
2018/0177604 A1\* 6/2018 Weiman .................... A61F 2/44
2019/0117409 A1\* 4/2019 Shoshtaev ............... A61F 2/447

\* cited by examiner

EXPANDABLE CAGE

CROSS-REFERENCE TO RELATED APPLICATIONS

This application claims the benefit of U.S. Provisional Application No. 62/687,308 filed Jun. 20, 2018, which is incorporated herein by reference.

FIELD

The present invention relates generally to the field of surgery, and more specifically, to an expandable intervertebral body fusion device (i.e., "cage") for placement in intervertebral space between adjacent vertebrae.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement. In surgical treatments, interbody implants may be used between adjacent vertebra, resulting in spinal fusion of the adjacent vertebra.

A fusion is a surgical method wherein two or more vertebrae are joined together (fused) by way of interbody implants, sometimes with bone grafting, to form a single bone. The current standard of care for interbody fusion requires surgical removal of all or a portion of the intervertebral disc. After removal of the intervertebral disc, the interbody implant is implanted in the interspace.

Interbody implants must be inserted into the intervertebral space in the same dimensions as desired to occupy the intervertebral space after the disc is removed. This requires that an opening sufficient to allow the interbody implant must be created through surrounding tissue to permit the interbody implant to be inserted into the intervertebral space. In some cases, the intervertebral space may collapse prior to insertion of the interbody implant. In these cases, additional hardware may be required to increase the intervertebral space prior to insertion of the implant.

In addition, minimally invasive surgical techniques may have been used on the spine. Under minimally invasive techniques, small incisions are done to access the intervertebral space. Through these incisions, discs are removed and an interbody implant is placed in the intervertebral disc space to restore normal disc height. Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

It would be desirable to insert an interbody implant into the intervertebral space at a first smaller dimension and once in place, deploy to a second, larger dimension to occupy the collapsed or reduced intervertebral space.

SUMMARY

Disclosed is an expandable intervertebral body fusion device (i.e., "expandable cage") that is configured to have an initial collapsed state having a first height and first width suitable for being inserted into an intervertebral space defined by a pair of adjacent vertebrae, and a final expanded state having a second height and second width that is greater than the first height. The implant may be expanded from the initial collapsed state to the expanded state in-situ. The expanded state increases the distance between the adjacent vertebrae and provides support to the adjacent vertebrae while bone fusion occurs and also provides rigid support between the adjacent vertebrae that withstands compressive forces. By inserting the expandable cage into the intervertebral space in the initial collapsed state, it is possible to perform the surgery percutaneously with minimal disruption to tissues surrounding the surgical site and intervening soft tissue structures.

DETAILED DESCRIPTION

Figure 1:
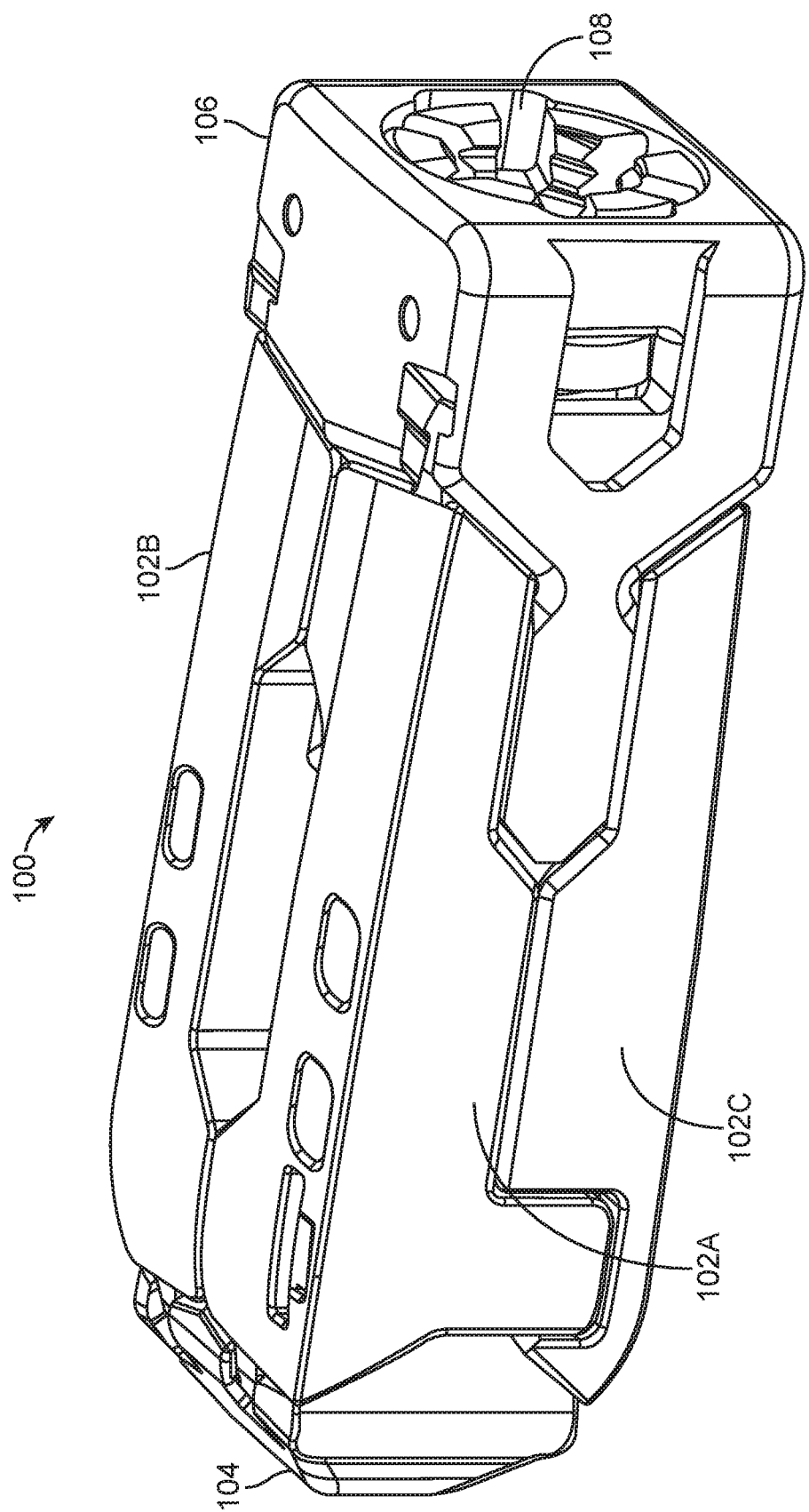
FIG. 1 is a perspective view showing an expandable cage in a collapsed state for introduction into disc space.
Figure 2:
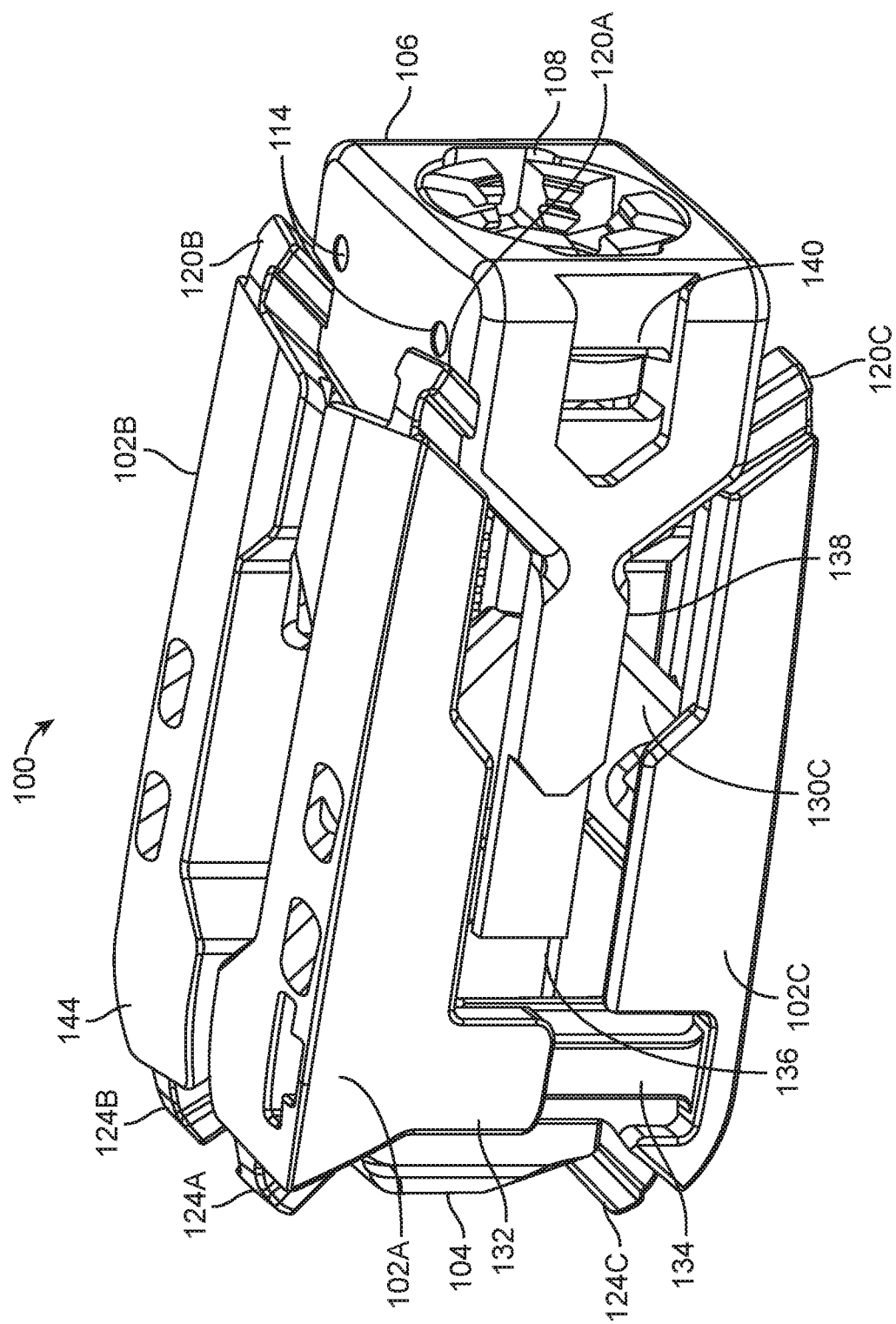
FIG. 2 is a perspective view showing the expandable cage of FIG. 1 in an expanded state.

The expandable intervertebral body fusion device cage includes a collapsed state and expanded state. The collapsed state allows insertion between the adjacent vertebrae with minimal dimensions. The expandable cage expands both vertically and horizontally by means of compound-angled ramps. Upper and lower end plates include slots, ramps and rails that engage a drive means that moves the upper and lower end plates both horizontally and vertically away from each other. In some embodiments, the upper and lower end plates are forced apart using corresponding compound-angled rails, slots and ramps on a frame and a drive housing (e.g., tongue-in-groove features, T-slots, or dovetails). Vertical rails may be couple the superior and inferior end plates to increase the stability of the device and horizontal rails may also be used to couple the frame to the drive housing to increase the rigidity of the device. The end plates may also be textured to promote bony integration.

The drive housing may include cutouts or other features to couple with an inserter instrument as well as holes for pins to hold the screw in place. The pins, may be made from a superelastic material like Nitinol, engage grooves in the head of the drive screw to both retain it and prevent it from loosening. A cannulation in the drive screw allows for post-filling of bone graft material after the cage is expanded. This cannulation features may include a thread that can be used by the inserter and removal tools for more positive engagement.

Referring now to FIGS. 1-7, an expandable cage 100 is shown that includes upper end plates 102A, 102B and lower end plates 102C, 102D coupled to a drive means. In the embodiment shown, the drive means includes a frame 104 and a drive housing 106 with drive mechanism, such as a drive screw 108. The upper and lower end plates 102A-102D include various compound-angled slots, ramps and rails that are designed to slidingly engage corresponding slots, ramps and rails on the frame 104 and drive housing 106 (discussed in more detail below). The slots, ramps and rails may be any suitable configuration that allow for the sliding movement between the components. For example, the ramps and rails may use a tongue-in-groove design, a T-slot design, a dovetail design, or a combination of designs.

The expandable cage 100 is movable between a collapsed state (shown in FIG. 1) to an expanded state (shown in FIG. 2) via the drive mechanism 108. In the embodiment shown, the drive mechanism 108 is a drive screw 108 that includes a distal end having threads 110 designed to engage a threaded portion 110 on a proximal end of the frame 104. As the drive screw 108 is turned in a first direction, the frame 104 and drive housing 106 move closer together, which moves the upper and lower end plates 102A-102D away from each other via the compound-angled slots, ramps and rails to expand the expandable cage 100 from the collapsed state to the expanded state. When the drive screw 108 is turned in a second direction, the frame 104 and drive housing 106 move further apart, collapsing the expandable cage 100 to the collapsed state. The drive screw 108 also may have a threaded portion 142 on the proximal end that is configured to engage inserter and removal tools (not shown). The drive screw 108 is held in the drive housing via a circumferential slot 112 configured to engage retention pins 114 positioned within retention pin holes 116 of the drive housing 106.

While a drive screw is shown, the drive mechanism 108 can be any mechanism capable of moving the frame 104 and drive housing 106 away from each other or toward each other to expand or collapse the expandable cage 100. Other types of drive mechanisms may include: a belt drive, rack and pinion drive, linear motor drive, ball screw drive, lead screw drive, or any other suitable drive.

While two upper end plates and two lower end plates are in the embodiment shown, other embodiments may include two or more upper end plates and two or more lower end plates. For example, there may be three upper and lower end plates, four upper and lower end plates, etc.

Figure 3B:
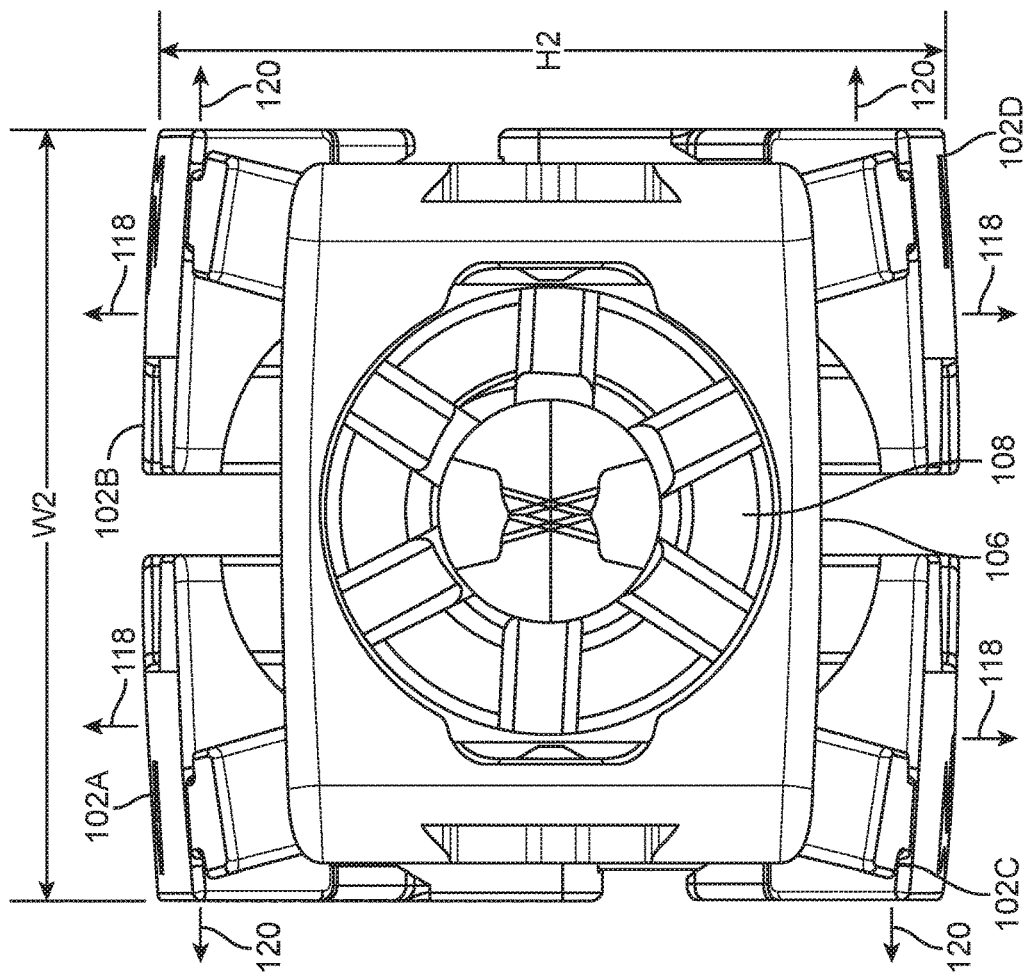
FIGS. 3A and 3B are proximal or front views of the expandable cage of FIG. 1 in collapsed and expanded states.
Figure 3A:
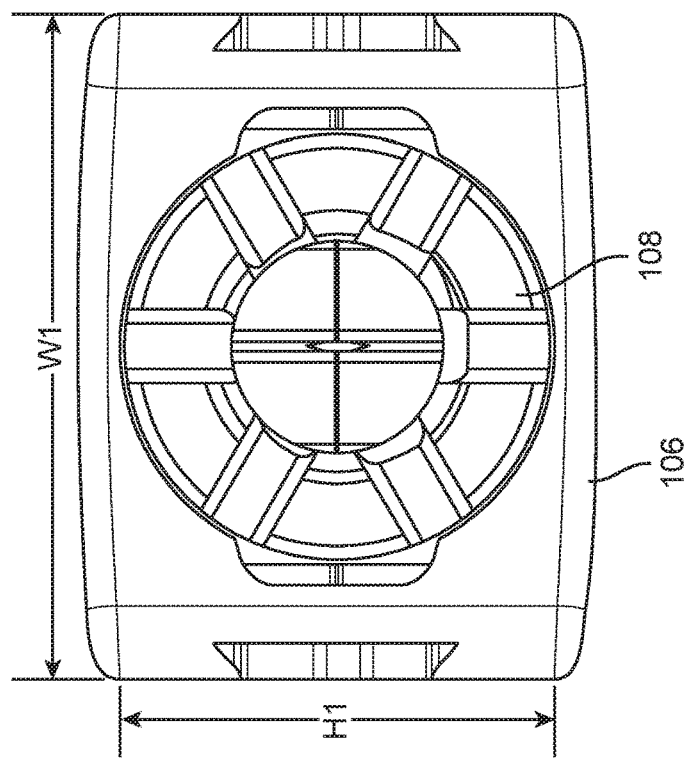

FIGS. 3A and 3B are proximal or front views of the expandable cage of in collapsed and expanded states. When the drive screw 108 is turned or rotated in the first direction, the frame 104 and drive housing 106 move toward each other and closer together, which moves the upper and lower end plates 102A-102D away from each other both vertically 118 and horizontally 120 to expand the expandable cage 100. The design of the compound-angled slots, ramps and rails between the components allow the upper end plates 102A-102B to vertically 118 move away from the lower end plates 102C-102D, and at the same time the upper end plates 102A-102B horizontally 120 move away from each other and the lower end plates 102C-102D horizontally 120 move away from each other, thereby expanding the expandable cage 100 both vertically and horizontally from the collapsed state (FIG. 3A) to the expanded state (FIG. 3B).

In the collapsed state the expandable cage 100 has a first height H1 and first width W1. When the screw 108 is rotated in a first direction, the frame 104 and drive housing 106 start moving toward each other and the end plates expand to a second height H2 and second width W2. The expandable cage 100 does not have to be completely extended to H2 and can be stopped anywhere between H1 and H2, depending on the expansion needed between the adjacent vertebrae.

Figure 4:
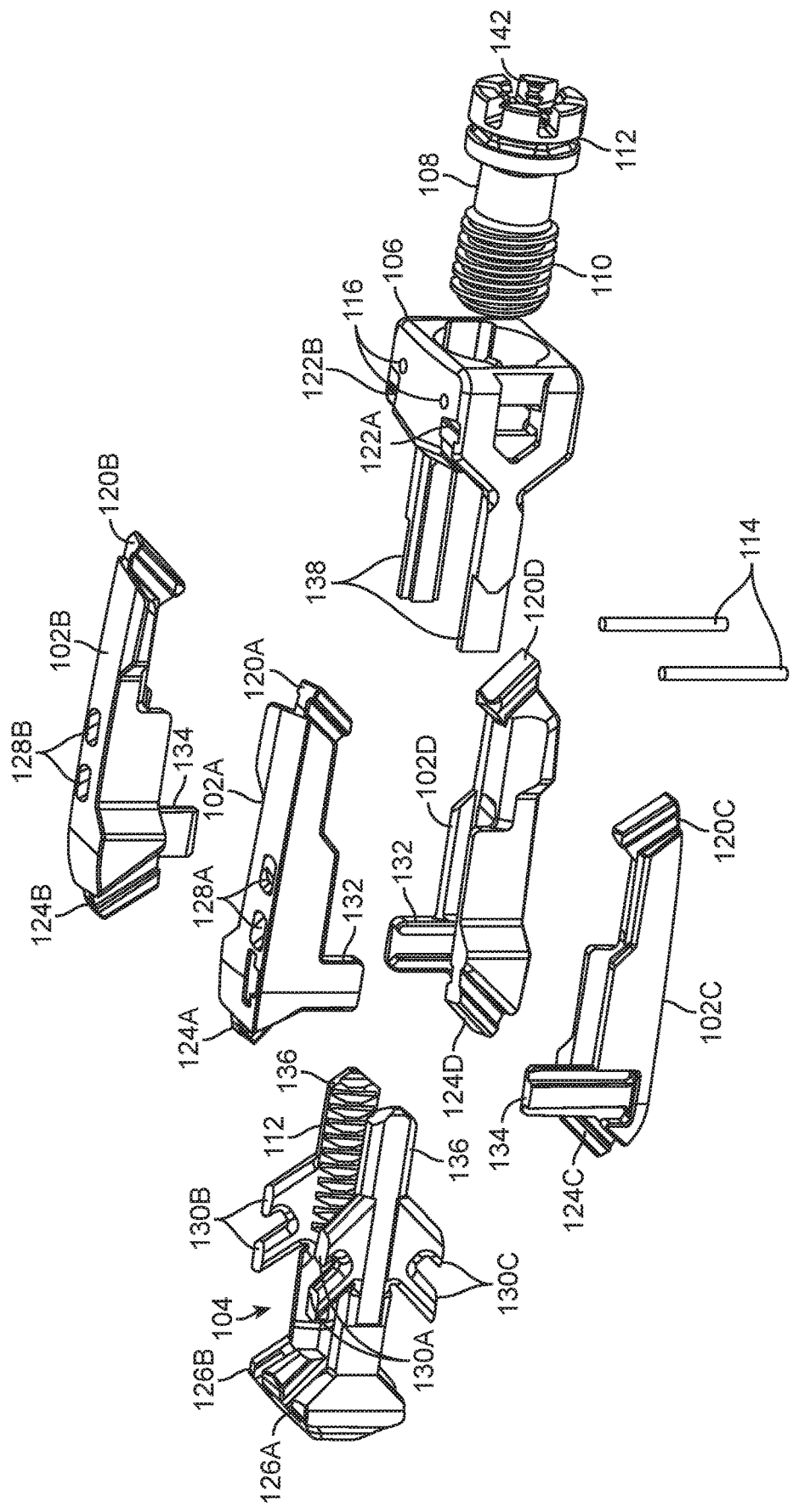
FIG. 4 is an exploded view showing the expandable cage of FIG. 1.
Figure 5:
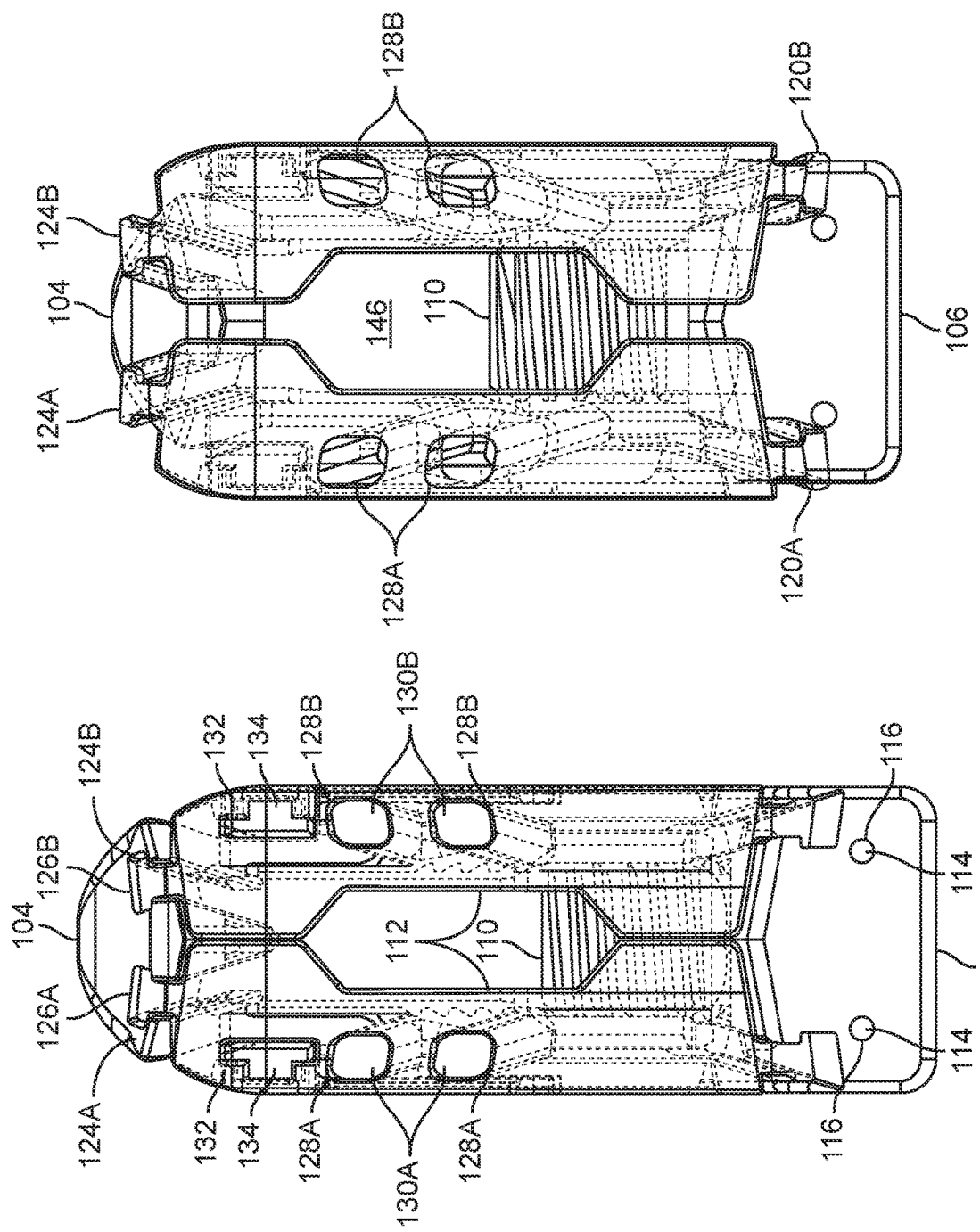
FIGS. 5A and 5B are top views showing the expandable cage of FIG. 1 in collapsed and expanded states with the end plates transparent.

FIG. 4 shows an exploded view of the expandable cage 100. As discussed above, the expansion of the expandable cage 100 uses corresponding compound-angled slot, ramps and rails between the components. The upper end plates 102A, 102B and lower end plates 102C, 102D include compound-angled rails 120A-120D located on the proximal ends and compound-angled rails 124A-124D located on the distal ends. The proximal compound-angled rails 120A-120D of the end plates slidably engage with compound-angled ramps 122A-122D in the drive housing 106 while the distal compound-angled rails 124A-124D slidably engage with compound-angled ramps 126A-126D in the frame 106.

In some embodiments, the upper and lower end plates 102A-102D also include one or more internal compound-angled slots or ramps 128A-128D that slidably engage corresponding compound-angled rails 130A-130D on the frame 104. The ramps 128A-128D and rails 130A-130D should have compatible compound-angles with the ramps and rails discussed above.

In some embodiments, the upper and lower end plates 102A-102D may also include slidably engageable vertical rails, slots or grooves to increase the stability of the expandable cage 100. For example, end plates 102A and 102C may have vertical slots or grooves 132 that slidably receive vertical rails 134 on end plates 102B and 102D.

In some embodiments, the upper and lower end plates may use the same design so that only two end plate configurations are needed. For example, in the embodiment shown in FIG. 4, upper end plate 102A and lower end plate 102C may be a first design, and upper end plate 102B and lower end plate 102D may be a second design. During assembly, the first design upper end plate 102A may be turned over and used as lower end plate 102C, and second design upper end plate 102B may be turned over and used as lower end plate 102D.

In some emblements, the frame 104 and drive housing 106 may include slidably engageable horizontal rails that are received within corresponding slots or grooves to increase the rigidity of the expandable cage 100. For example, frame 104 may include horizontal rails 136 on the proximal end that slidably engage horizontal slots or grooves 138 on the distal end of the drive housing 106. As the drive screw 108 is turned, the horizontal rails 136 slide within the horizontal slots or grooves 138.

The drive housing 106 may also include features that couple with inserter instruments. For example, in the embodiment shown, the drive housing 106 includes cutouts 140 for inserter instruments (not shown).

In the expanded state the expandable cage 100 includes a central opening 146 that may be filled with materials, such as bone graft, allograft, Demineralized Bone Matrix ("DBM") or other suitable materials. To insert the materials, in some embodiments the drive screw 108 may be cannulated to allow materials to be introduced into the central opening 146 of expandable cage 100 once is place in desired position. The cannulated drive screw 106 may allow the post filling of bone graft or other materials after the expandable cage 100 has been expanded. The cannulated feature of the drive screw 108 may include a thread 142 on the proximal end. The thread 142 may be used to engage the inserter tool and/or removal tool for more positive engagement (not shown).

The end plates 102A-102D may include surface features 144 configured to promote bone growth that engage the bone. For example, the surface may be a textured surface or roughened surface to promote bone integration or the surface may use a coating or be chemically etched to form a porous or roughened surface. In some embodiments, the surface 144 may include teeth. The end plates 102A-102D may use the same teeth or the teeth may be different for each end plate. For example, the teeth on the top end plates 102A, 102B may have different spacing, configuration, thickness, height, and width, as well as angles of orientation with respect to the teeth on the lower end plates 102C, 102D.

FIGS. 5A and 5B are top views of the expandable cage 100 in the collapsed state (5A) and expanded state (5B). The end plates 102A-102D are transparent to illustrate the relationship of the components.

Figure 6:
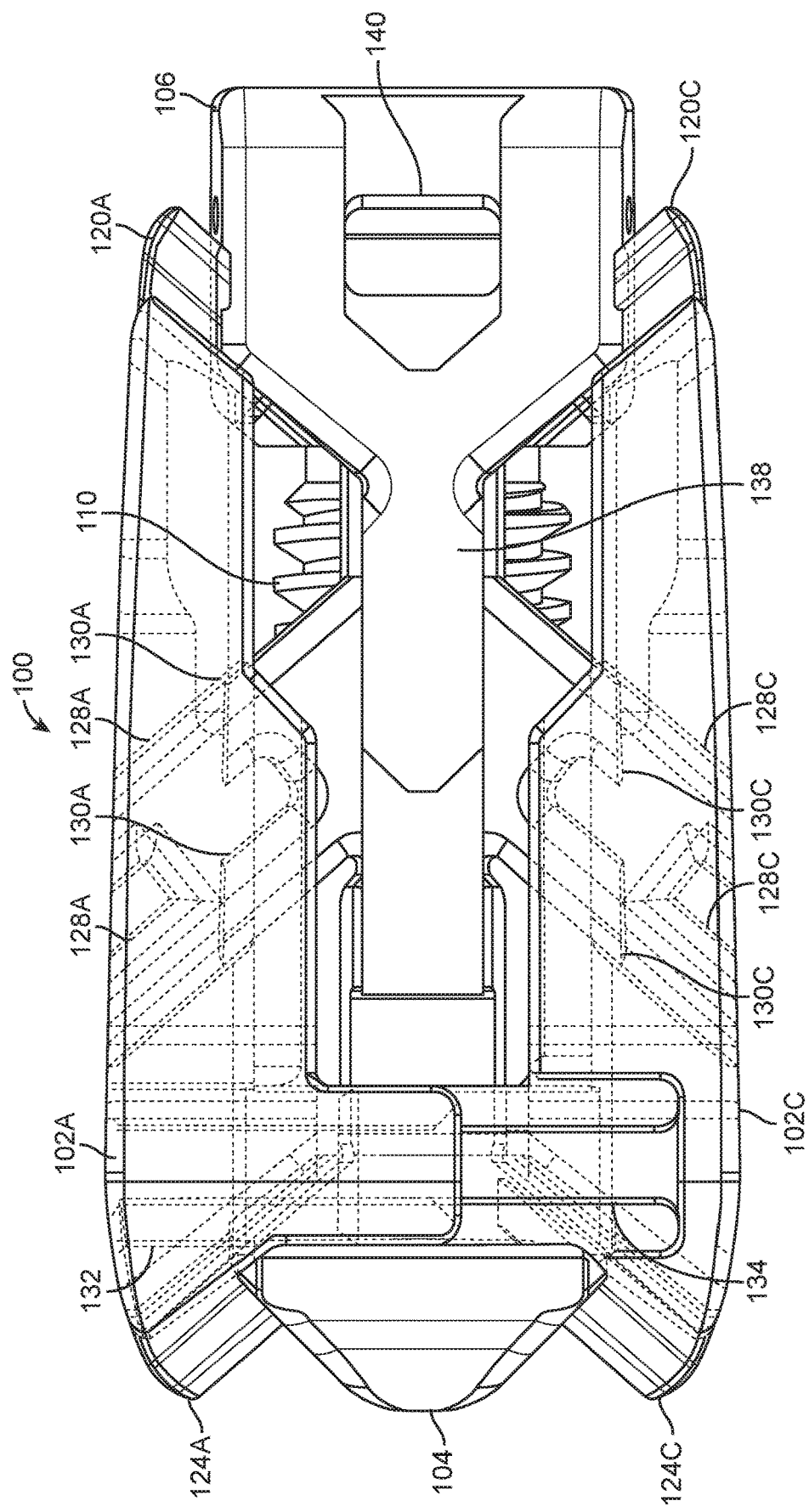
FIG. 6 is a side view showing the expandable cage of FIG. 1 in the expanded state with the end plates transparent.

FIG. 6 is a side view of the expandable cage 100 in the expanded state. The end plates 102A-102D are transparent to illustrate the relationship of the components.

Figure 7:
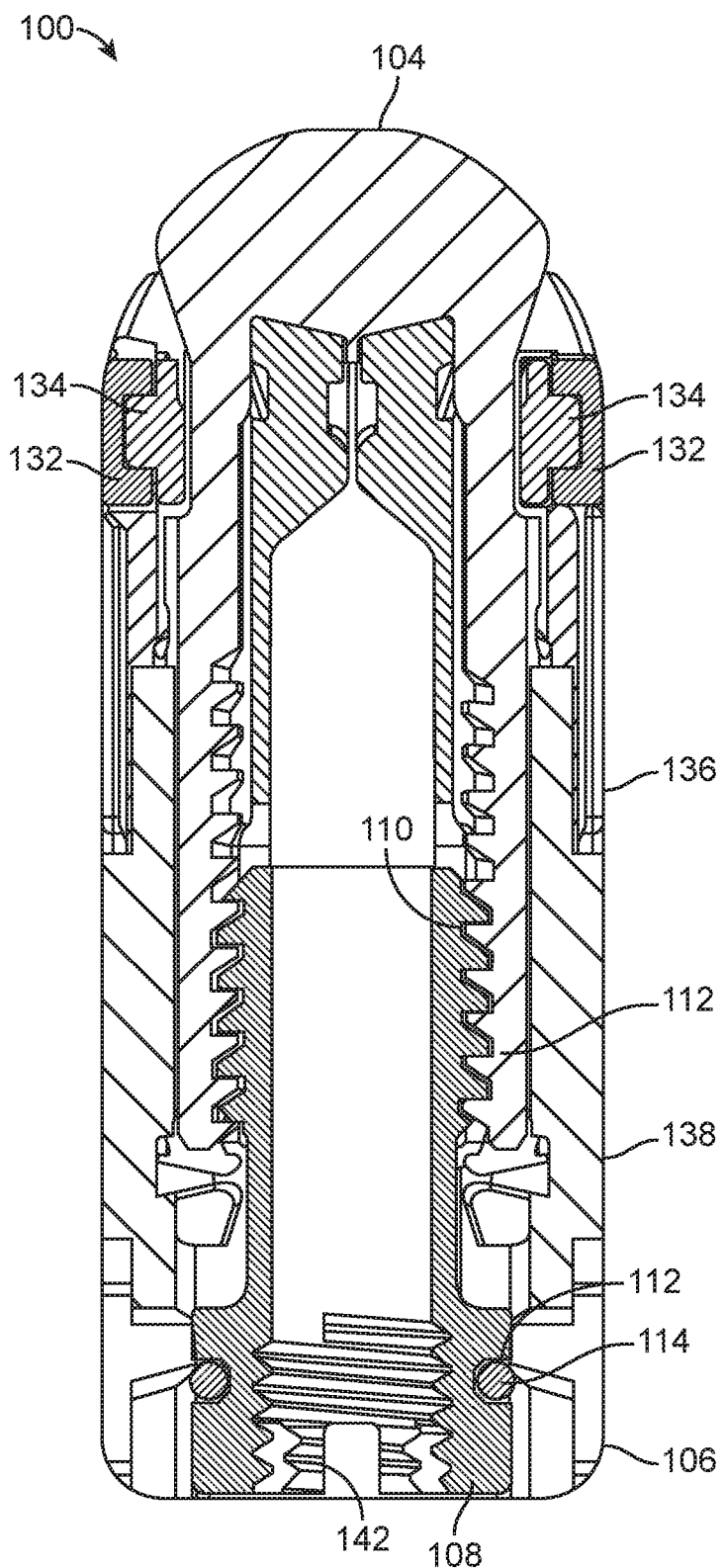
FIG. 7 is a top view of midplane cross-section showing the interfaces between the components.

FIG. 7 is a midplane cross-sectional view of the expandable cage 100 in the collapsed state showing the interfaces between the components.

Figure 8:
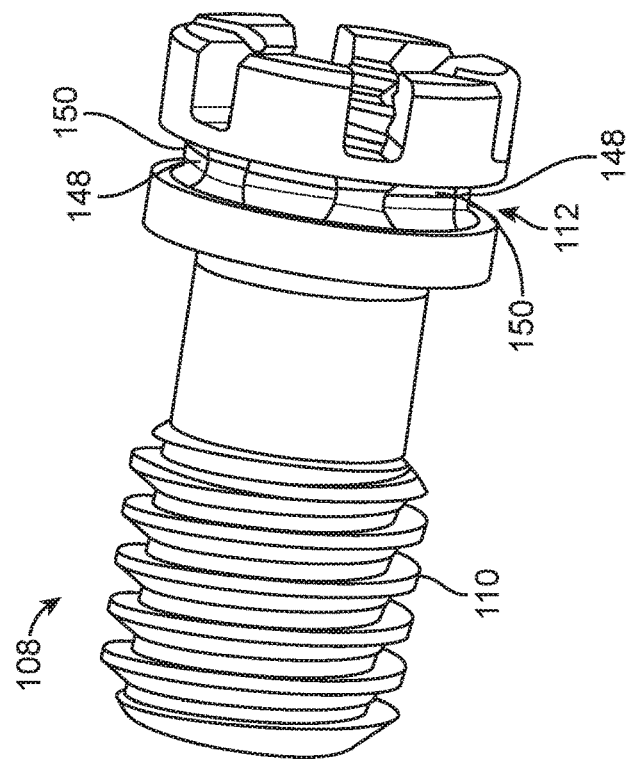
FIG. 8 is a perspective view of the drive screw showing the circumferential slot having grooves to prevent loosening.

FIG. 8 is a perspective view showing detail anti-loosening feature of the drive screw 108. As discussed above, the circumferential slot 112 is configured to engage retention pins 114 positioned within retention pin holes 116 of the drive housing 106 to keep the drive screw 108 within the drive housing 106. In the embodiment shown, the lower part of the circumferential slot 112 includes flat surfaces creating high spots 148 and low spots 150 that engage the retention pins 114.

Figure 9:
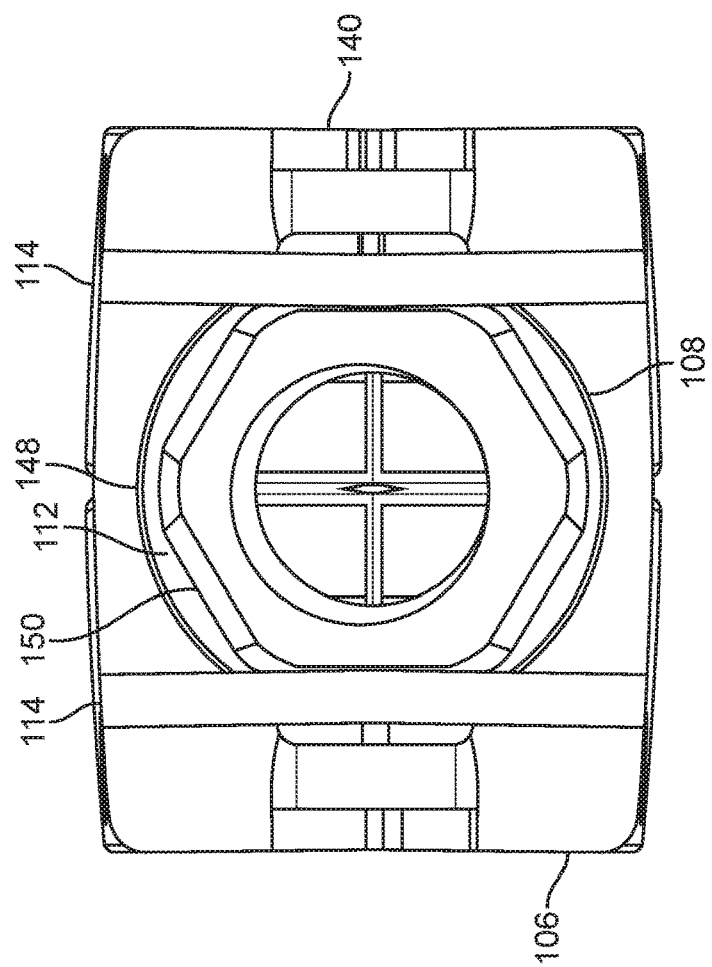
FIG. 9 is a front cross-section view through the retention pins, illustrating engagement with drive screw grooves to prevent loosening.

FIG. 9 is a front cross-section view through the retention pins 144, illustrating engagement of the retention pins 144 with drive screw circumferential slot or groove 112 to prevent loosening of the drive screw 108 within the drive housing 106 (i.e., "anti-loosening" mechanism). The pins 144 are made of flexible material, such as Nitinol, configured to interface with the high spots 148 and low spots 150 on the screw. When the drive screw 108 is turned, the elastic retention pins 144 flexes outward at each high spot 148 as it passes producing resistance/friction. When the elastic retention pins 144 engage the low spots 150, this friction is what resists rotation of the driver screw "loosening".

In use, the screw 108 engages the threads 112 on the frame 104 such that when it is rotated, the frame 104 translates toward the drive housing 106, moving the end plates 102A-102D from the collapsed state to the expanded state. If desired, the screw 108 may be rotated in the opposite direction to translate the frame 104 away the drive housing 106, moving the end plates 102A-102D from the expanded state back to the collapsed state. This allows the expandable cage 100 to be moved to another location or reposition if it is expanded in the wrong location and needs to be collapsed prior to moving or repositioning.

The expandable cage 100 components may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, surfaces on the components may be formed of a porous material that participates in the growth of bone with the adjacent vertebral bodies. In some embodiments, the components may include a roughened surface that is coated with a porous material, such as a titanium coating, or the material is chemically etched to form pores that participate in the growth of bone with the adjacent vertebra. In some embodiments, only portions of the components be formed of a porous material, coated with a porous material, or chemically etched to form a porous surface, such as the upper and lower surfaces 144 that contact the adjacent vertebra are roughened or porous.

The expandable cage 100 may also be used with various tools, such as inserter tools, deployment tools and/or removal tools. The tools may include various attachment features to enable percutaneous insertion of the expandable cage 100 into the patient. For example, the tools may include arms or clamps to attach to the cutouts or other openings, slots or trenches of the drive mechanism. The tools may also include an actuation device to couple with the proximal section of the screw 108. Once the expandable cage 100 has been inserted and positioned within the intervertebral space between two vertebrae with the insertion tool, the deployment tool may actuate to deploy and expand the expandable cage 100 by applying a rotational force to screw 108. The deployment tool may also be cannulated to introduce materials into the expandable cage 108.

In operation, the expandable cage 100 may be inserted into the intervertebral disc space between two vertebrae using an insertion tool. In some cases, the disc space may include a degenerated disc or other disorder that may require a partial or complete discectomy prior to insertion of the expandable cage 100. The deployment tool may engage with the proximal end of the expandable cage 100. As the deployment tool applies the rotational force, the expandable cage 100 gradually expands as described above. In some cases, the expandable cage 100 may need to be removed with a removal tool.

In some embodiments, more than one expandable cage 100 can be implanted between the adjacent vertebrae of the patient. In such embodiments, multiple expandable cages 100 can be placed in a side-by-side configuration or any other suitable configuration, thereby creating additional support.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An expandable cage for placement between adjacent vertebrae comprising:
   two or more upper end plates having compound-angled slots, ramps or rails;
   two or more lower end plates having compound-angled slots, ramps or rails; and
   drive means having corresponding compound-angled slots, ramps or rails configured to slidingly engage the compound-angled slots, ramps or rails of the two or more upper and lower end plates and slidably engageable horizontal rails that are slidably received within corresponding horizontal slots or grooves to increase the rigidity of the expandable cage;
   wherein movement of the drive means in a first direction moves the two or more upper and lower end plates away from each other both vertically and horizontally to expand both a height and a width of the expandable cage from a collapsed state to an expanded state.

2. The expandable cage of claim 1, wherein movement of the drive means in a second direction moves the two or more upper and lower end plates toward each other collapsing the expandable cage to the collapsed state.

3. The expandable cage of claim 1, wherein the corresponding compound-angled slots, ramps or rails may be any suitable configuration that allows for the sliding movement between the two or more upper and lower end plates.

4. The expandable cage of claim 3, wherein the compound-angled slots, ramps or rails configuration between the two or more upper and lower end plates is a tongue-in-groove design.

5. The expandable cage of claim 3, wherein the compound-angled slots, ramps or rails configuration between the two or more upper and lower end plates is a T-slot design.

6. The expandable cage of claim 3, wherein the compound-angled slots, ramps or rails configuration between the two or more upper and lower end plates is a dovetail design.

7. The expandable cage of claim 1, wherein the two or more upper and lower end plates also include slidably engageable vertical rails that are slidably received within corresponding vertical slots or grooves to increase the stability of the expandable cage.

8. The expandable cage of claim 1, wherein the compound-angled slots, ramps or rails are positioned on a proximal end and a distal end of the two or more upper and lower end plates.

9. The expandable cage of claim 1, wherein the compound-angled slots, ramps or rails are internal compound-angled slots, ramps or rails positioned between a proximal end and a distal end of the two or more upper and lower end plates.

10. The expandable cage of claim 1, wherein the drive means includes a frame and a drive housing coupled to a drive mechanism, wherein the frame and drive housing include the corresponding compound-angled slots, ramps or rails configured to slidingly engage the compound-angled slots, ramps or rails of the two or more upper and lower end plates.

11. The expandable cage of claim 10, wherein actuation of the drive mechanism moves the frame and drive housing toward or away from each other to move the two or more first and second lower end plates.

12. The expandable cage of claim 1, wherein the two or more upper end plates include first and second upper end plates and the two or more lower end plates include first and second lower end plates.

13. An expandable cage for placement between adjacent vertebrae comprising:
    two or more upper end plates having compound-angled slots, ramps or rails;
    two or more lower end plates having compound-angled slots, ramps or rails; and
    drive means comprising a frame and a drive housing coupled with a drive mechanism, the frame and drive housing having corresponding compound-angled slots, ramps or rails configured to engage the compound-angled slots, ramps or rails of the two or more upper and lower end plates and slidably engageable horizontal rails that are slidably received within corresponding horizontal slots or grooves to increase the rigidity of the expandable cage;
    wherein movement of the drive mechanism in a first direction moves the frame and drive housing toward each other and the two or more upper and lower end plates away from each other both vertically and horizontally via the compound-angled ramps or rails, thereby expanding both a height and a width of the expandable cage from a collapsed state to an expanded state.

14. The expandable cage of claim 13, wherein the compound-angled slots, ramps or rails are positioned on a proximal end and a distal end of the upper and lower end plates.

15. The expandable cage of claim 13, wherein the compound-angled slots, ramps or rails are internal compound-angled slots, ramps or rails positioned between a proximal end and a distal end of the two or more upper and lower end plates.

16. The expandable cage of claim 13, wherein the two or more upper and lower end plates also include slidably engageable vertical rails that are slidably received within corresponding vertical slots or grooves to increase the stability of the expandable cage.

* * * * *